(12) United States Patent
Mazor et al.

(10) Patent No.: US 6,351,516 B1
(45) Date of Patent: Feb. 26, 2002

(54) DETECTION OF VOIDS IN SEMICONDUCTOR WAFER PROCESSING

(75) Inventors: Isaac Mazor, Haifa (IL); Long Vu, Round Rock, TX (US)

(73) Assignee: Jordan Valley Applied Radiation Ltd., Migdal Haemek (IL)

( * ) Notice: Subject to any disclaimer, the term of this patent is extended or adjusted under 35 U.S.C. 154(b) by 0 days.

(21) Appl. No.: 09/461,670

(22) Filed: Dec. 14, 1999

(51) Int. Cl.[7] .............................................. G01N 23/223
(52) U.S. Cl. ............................................. 378/44; 378/45
(58) Field of Search .......................... 378/44, 45, 49, 378/50, 48; 437/197, 198, 199

(56) References Cited

U.S. PATENT DOCUMENTS

| | | | |
|---|---|---|---|
| 4,169,228 A | * 9/1979 | Briska et al. | 250/272 |
| 4,551,905 A | * 11/1985 | Chao et al. | 29/571 |
| 5,365,563 A | * 11/1994 | Kira et al. | 378/48 |
| 5,385,867 A | * 1/1995 | Ueda et al. | 437/195 |
| 5,497,008 A | * 3/1996 | Kumakhov | 250/505.1 |
| 5,877,498 A | * 3/1999 | Sugimoto et al. | 250/310 |
| 5,893,758 A | * 4/1999 | Sandhu et al. | 438/708 |
| 5,937,027 A | * 8/1999 | Satohs | 378/44 |
| 6,001,736 A | * 12/1999 | Kondo et al. | 438/677 |
| 6,108,398 A | * 8/2000 | Mazor et al. | 378/45 |

FOREIGN PATENT DOCUMENTS

| | | | | |
|---|---|---|---|---|
| JP | 06283585 A | * 10/1994 | | H01L/21/66 |
| JP | 07019844 A | * 2/1997 | | G01N/23/223 |

OTHER PUBLICATIONS http://www.semiconductoronline.com.

* cited by examiner

*Primary Examiner*—Robert H. Kim
*Assistant Examiner*—Irakli Kiknadze
(74) *Attorney, Agent, or Firm*—Christie, Parker & Hale, LLP

(57) ABSTRACT

A method for testing the deposition and/or the removal of a material within a recess on the surface of a sample. An excitation beam is directed onto a region of the sample in a vicinity of the recess, and an intensity of X-ray fluorescence, emitted from the region in a spectral range in which the material is known to fluoresce, is measured. A quantity of the material that is deposited within the recess is determined responsive to the measured intensity.

21 Claims, 3 Drawing Sheets

DETECTION OF VOIDS IN SEMICONDUCTOR WAFER PROCESSING

FIELD OF THE INVENTION

The present invention relates generally to methods and apparatus for non-destructive testing, and specifically to testing of thin film layers formed in the production of semiconductor devices.

BACKGROUND OF THE INVENTION

Integrated circuit manufacturers face constant demands to reach higher component densities and faster clock speeds. In response to these demands, the critical dimensions of lithographic patterns formed on semiconductor wafers have been steadily reduced. Moreover, copper, because of its high conductivity and better electromigration properties, has begun to replace aluminum as the conducting material of choice for the metal layers of semiconductor devices. The chemical and physical properties of copper, however, create new problems that must be addressed in the manufacturing process. These problems are exacerbated by the decreasing critical dimensions of the features produced on the wafer.

FIG. 1 is a schematic, sectional illustration of a detail of a semiconductor wafer 20, showing one of the serious problems that can arise in wafer processing. In this illustration, an inter-layer dielectric (ILD) 24 is formed on a silicon substrate 22. Typically, the ILD comprises silicon dioxide or other low-K insulating materials. A feature such as a via 32 (i.e., a recess) is formed in layer 24 by a photolithographic process, as is known in the art, and is to be filled with a conductor, typically copper or tungsten. Although the figure shows a gap between the bottom of via 32 and substrate 22, in practice the width of this gap may be effectively zero. As a consequence of the small critical dimensions used in the photolithography, via 32 has a high aspect ratio, i.e., its height is as great as or greater than its width.

In preparation for filling the via with copper, a barrier layer 26 is first deposited over ILD 24, in order to prevent penetration of copper into the ILD. Layer 26 typically comprises tantalum. The barrier layer must be made thick enough at all points to withstand copper penetration, but not so thick as to unduly reduce the quantity of copper to be deposited in the via. A thin seed layer 28, typically comprising copper, is deposited over barrier layer 26, and the remaining volume of via 32 is filled with copper, typically by electroplating or physical vapor deposition (PVD).

Via 32 should be filled completely by the copper in layer 26. Any deficiency in filling the via will compromise the performance of the device being manufactured. Unfortunately, variations in wafer processing parameters, such as a deviation from a specified pressure and/or temperature while the via is being filled with copper, may lead to the formation of a void 34 within the via. Voids may similarly occur in other recessed structures on the wafer, such as trenches and contact structures. Such embedded voids are virtually impossible to detect by non-destructive defect inspection methods known in the art, such as optical or scanning electron microscope (SEM) surface inspection. The known methods that are commonly available for finding and evaluating voids, such as SEM or TEM in conjunction with cross-sectioning or with a focused ion beam, are destructive, requiring at least local destruction of the wafer under test, and are time-consuming and costly.

SUMMARY OF THE INVENTION

It is an object of the present invention to provide improved methods and apparatus for non-destructive testing of semiconductor wafers in production.

It is a further object of some aspects of the present invention to provide methods and apparatus for detection of voids formed within microelectronic devices in production.

It is yet a further object of some aspects of the present invention to provide methods and apparatus for verifying the thickness of layers deposited on a semiconductor wafer in the course of production.

In some preferred embodiments of the present invention, a test pattern is formed in a surface layer of a semiconductor wafer, for use in verifying the volume of material deposited within recesses on the wafer. The pattern serves particularly to ascertain whether or not voids have occurred in the volume of deposited material. Preferably, the surface layer of the wafer comprises a dielectric layer, in which the pattern is formed by photolithography. Most preferably, the pattern is formed on a scribe line of the wafer. The test pattern comprises a test region and, preferably, a reference region. The test region has multiple recesses formed in the surface layer, which are similar in critical dimensions and aspect ratio to recesses, such as vias, that are formed in functional areas of the wafer. The reference region preferably has no such recesses. In a subsequent process stage, when the vias on the wafer are filled with the next layer of material, typically a metal layer, such as copper, the recesses in the test region are similarly filled. Thus, if voids or other irregularities form within the vias, there are likely to be similar voids or irregularities in the recesses of the test region.

An X-ray microfluorescence analyzer, comprising an excitation source and one or more detectors, is used to determine whether the recesses of the test pattern have been properly filled. When irradiated by the excitation source, the metal layer (or other fill material in the recesses) emits fluorescent X-rays with a characteristic spectrum. The intensity of this emission is proportional to the mass of the emitting material. The X-ray analyzer measures the intensity of the characteristic spectral emission from the test region, preferably by comparison to emission from the reference region. The intensity of the emission from the test region provides an indication of the volume of the metal in that region, i.e., of the quantity of metal filling the recesses. Should the intensity from the test region differ significantly from an expected value, it is an indication that the metal layer has deviated from the proper thickness or volume. In particular, if significant voids have formed inside the metal within the recesses, the emission intensity from the test region will be substantially lower than it would be otherwise. Based on such intensity variations, the X-ray analyzer identifies situations in which voids are suspected to exist, substantially without destructive effects on the wafer.

In other preferred embodiments of the present invention, X-ray microfluorescence measurements are made in an active device area of the wafer, in addition to or instead of measurements made on the test region described above. The measured fluorescence intensity is analyzed in a manner similar to that described above in order to determine whether voids have formed in filled recesses in the device area. Making these measurements on the device area, rather than in the test region, can also provide other essential information about the manufacturing process, such as step coverage and thickness uniformity at the device level for both materials deposition and removal stages.

Although preferred embodiments are described herein with particular reference to void detection in semiconductor wafer processing, it will be appreciated that the principles of the present invention may similarly be applied to detect other types of process faults, as well. These principles are applicable in substantially any situation in which the condition of a material layer inside a recess must be diagnosed, wherein the geometrical characteristics of the recess make other non-destructive testing methods, such as optical methods, unworkable or impractical.

There is therefore provided, in accordance with a preferred embodiment of the present invention, a method for testing the deposition and/or the removal of a material within a recess on the surface of a sample, including:

directing an excitation beam onto a region of the sample in a vicinity of the recess;

measuring an intensity of X-ray fluorescence emitted from the region in a spectral range in which the material is known to fluoresce; and determining a quantity of the material that is deposited within the recess responsive to the measured intensity.

Preferably, determining the quantity of the material within the recess includes detecting a void formed within the material in the recess. Alternatively or additionally, determining the quantity of the material includes determining a thickness of a layer of the material deposited in the recess.

Preferably, directing the excitation beam includes directing the beam at a test region and a reference region of the sample, and measuring the intensity of X-ray fluorescence includes comparing the fluorescence from the test region to fluorescence received from the reference region. Most preferably, the test region contains the recess, and the reference region has substantially no recesses in its surface.

Preferably, determining the quantity of the material includes analyzing the measured fluorescence responsive to a known depth of the recess.

In a preferred embodiment, the sample includes a semiconductor wafer, and the recess includes a microscopic recess etched into the surface of the wafer. Preferably, the material deposited in the recess includes a metal. Further preferably, irradiating the region includes irradiating a pattern of recesses formed in a test region on the wafer so as to determine how completely the metal has filled vias etched into the surface of the wafer.

There is also provided, in accordance with a preferred embodiment of the present invention, apparatus for testing the deposition of a material within a recess on the surface of a sample, including:

an excitation source, configured to direct an excitation beam onto a region of the sample in a vicinity of the recess;

one or more X-ray detectors, configured to receive X-ray fluorescence emitted from the region, and to generate signals responsive to the received fluorescence; and a processor, coupled to receive the signals from the one or more detectors and to measure, responsive to the signals, an intensity of the fluorescence in a spectral range in which the material is known to fluoresce, so as to determine a quantity of the material that is deposited within the recess.

Preferably, the excitation source includes an X-ray source with X-ray optics, which focus irradiation from the source onto the region. Most preferably, the apparatus is further configured to translate a focal point of the irradiation over the surface of the sample.

There is further provided, in accordance with a preferred embodiment of the present invention, a semiconductor wafer, including a surface layer in which a test pattern is formed, the test pattern including.

a test region, having a plurality of recesses formed in a surface layer thereof, in which recesses a material is deposited during production of semiconductor devices on the wafer; and a reference region, substantially without recesses.

The present invention will be more fully understood from the following detailed description of the preferred embodiments thereof, taken together with the drawings in which:

DETAILED DESCRIPTION OF PREFERRED EMBODIMENTS

Figure 2:
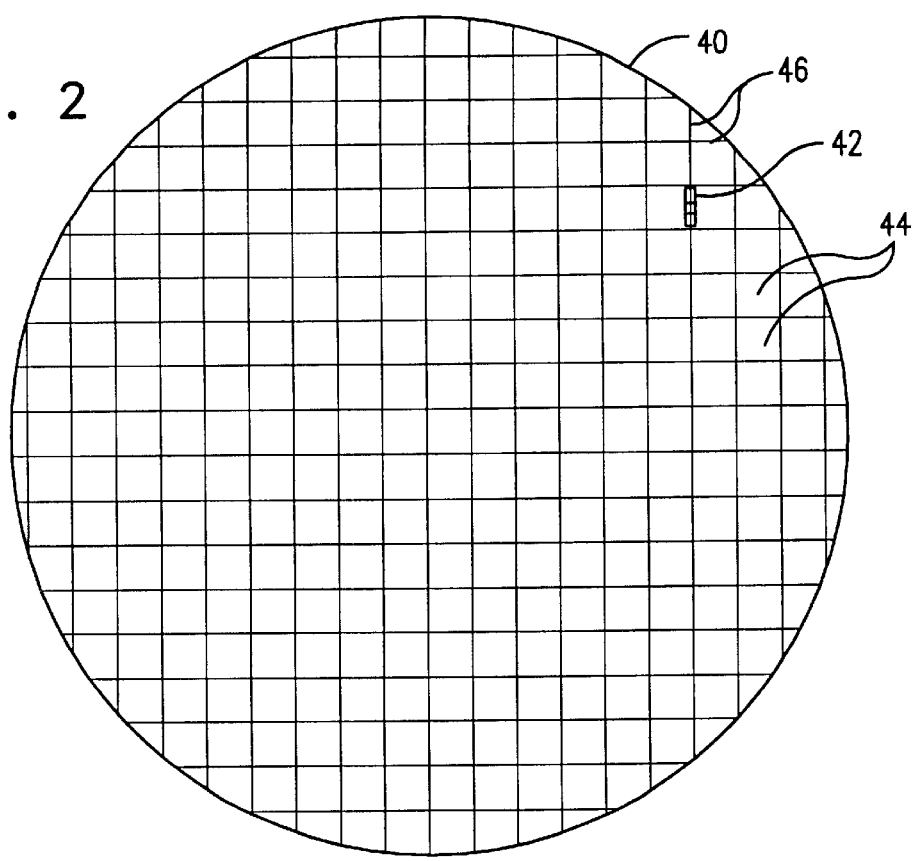
FIG. 2 is a schematic top view of a semiconductor wafer having a test pattern formed thereon, in accordance with a preferred embodiment of the present invention.

Reference is now made to FIG. 2, which is a schematic top view of a semiconductor wafer 40, typically a silicon wafer, on which a test pattern 42 is formed, in accordance with a preferred embodiment of the present invention. The wafer is divided into multiple dice 44, which are separated by scribe lines 46. Preferably, pattern 42 is positioned on one of the scribe lines, and is narrow enough, typically on the order of 75 μm, so as not to impinge significantly on the dice to either side of the line optionally, multiple patterns like pattern 42 are formed on different areas of wafer 40 to enable more thorough and/or varied testing.

Figure 1:
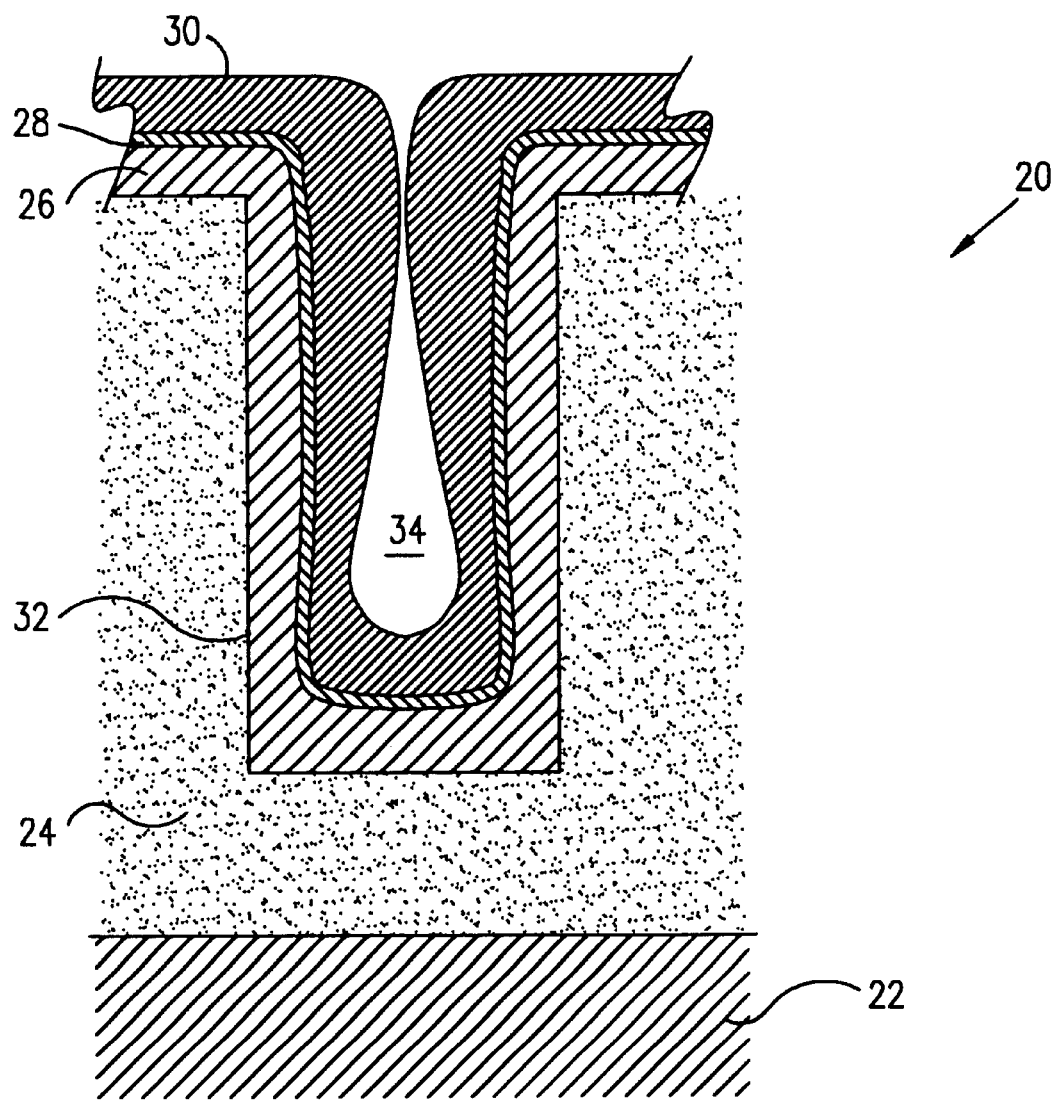
FIG. 1 is a schematic, sectional clustration showing a detail of a microelectronic device in production on a semiconductor wafer, useful in understanding an application of the present invention.
Figure 3A:
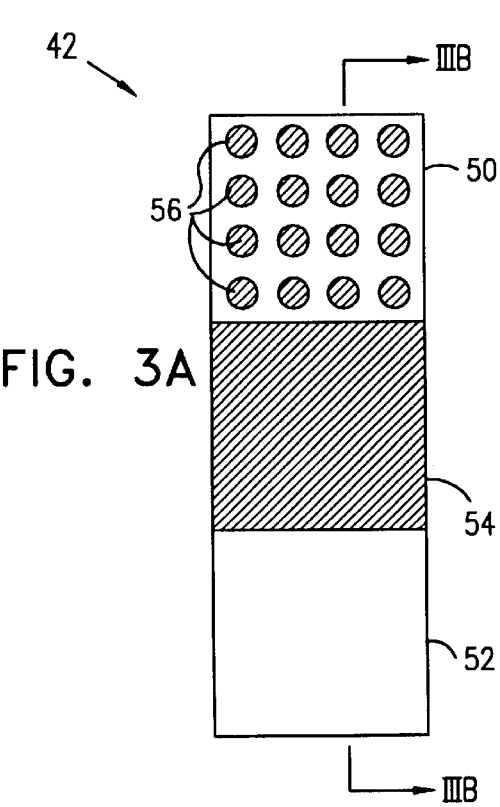
FIGS. 3A and 3B are top and sectional views, respectively, showing details of the test pattern of FIG. 2, in accordance with a preferred embodiment of the present invention.
Figure 3B:
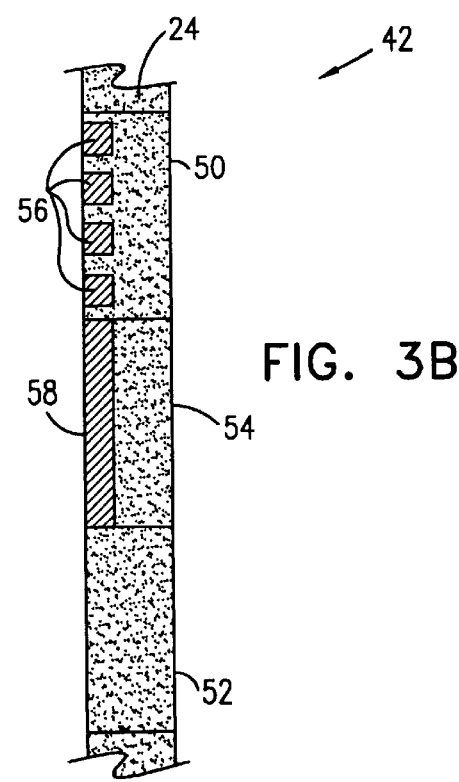

FIGS. 3A and 3B schematically show details of pattern 42 in top and sectional views, respectively, in accordance with a preferred embodiment of the present invention. The pattern is preferably formed in an appropriate stage of processing water 40, along with functional device features on dice 44, using photolithographic techniques, as are known in the art. In the present embodiment, the pattern is formed in a dielectric layer, such as in layer 24, shown in FIG. 1. Alternatively, the pattern may be produced in substantially any layer that is formed and etched, or otherwise patterned, on the surface of the wafer. Preferably, pattern 42 is formed on a portion of wafer 40 with a clear substrate, i.e., without layers underlying the pattern that could confuse the measurements described hereinbelow.

Pattern 42 comprises three regions, which are preferably mutually-adjoining, as shown in the figure, or in close proximity one to another, and are preferably formed over a clear area of the wafer substrate:

A test region 50, comprising a plurality of recesses 56. After the recesses have been etched, they are filled with another material or materials, in the same process steps and at the same time as vias and other recesses among the device features on dice 44 are filled. Thus, recesses 56 in region 50 are typically filled with multiple layers, such as barrier layer 26 and copper layers 28 and 30 (FIG. 1), but for the sake of simplicity, these multiple layers are not explicitly shown in FIG. 3B. Any defects, such as void 34, that may occur in nearby device features due to improper filling of vias and other recesses are likely to occur, as well, in recesses 56.

A zero reference region 52. This region contains substantially none of the fill material.

A full-scale reference region 54. This region has a full coating 58, to a known depth, of the material, such as copper, with which recesses 56 are filled.

The significance of these regions is described further hereinbelow. It is noted, however, that the shapes and configurations of the regions shown in FIGS. 3A and 3B have been chosen only by way of illustration. Other arrangements of the regions, as well as other shapes and arrangements of recesses 56, will be apparent to those skilled in the art. Furthermore, although the use of regions 52 and 54 is useful in enhancing the accuracy of measurements made on test pattern 42, these regions are not essential, and one or both of them may be omitted. It is also possible to use reference regions that are not located on the wafer under test.

Figure 4:
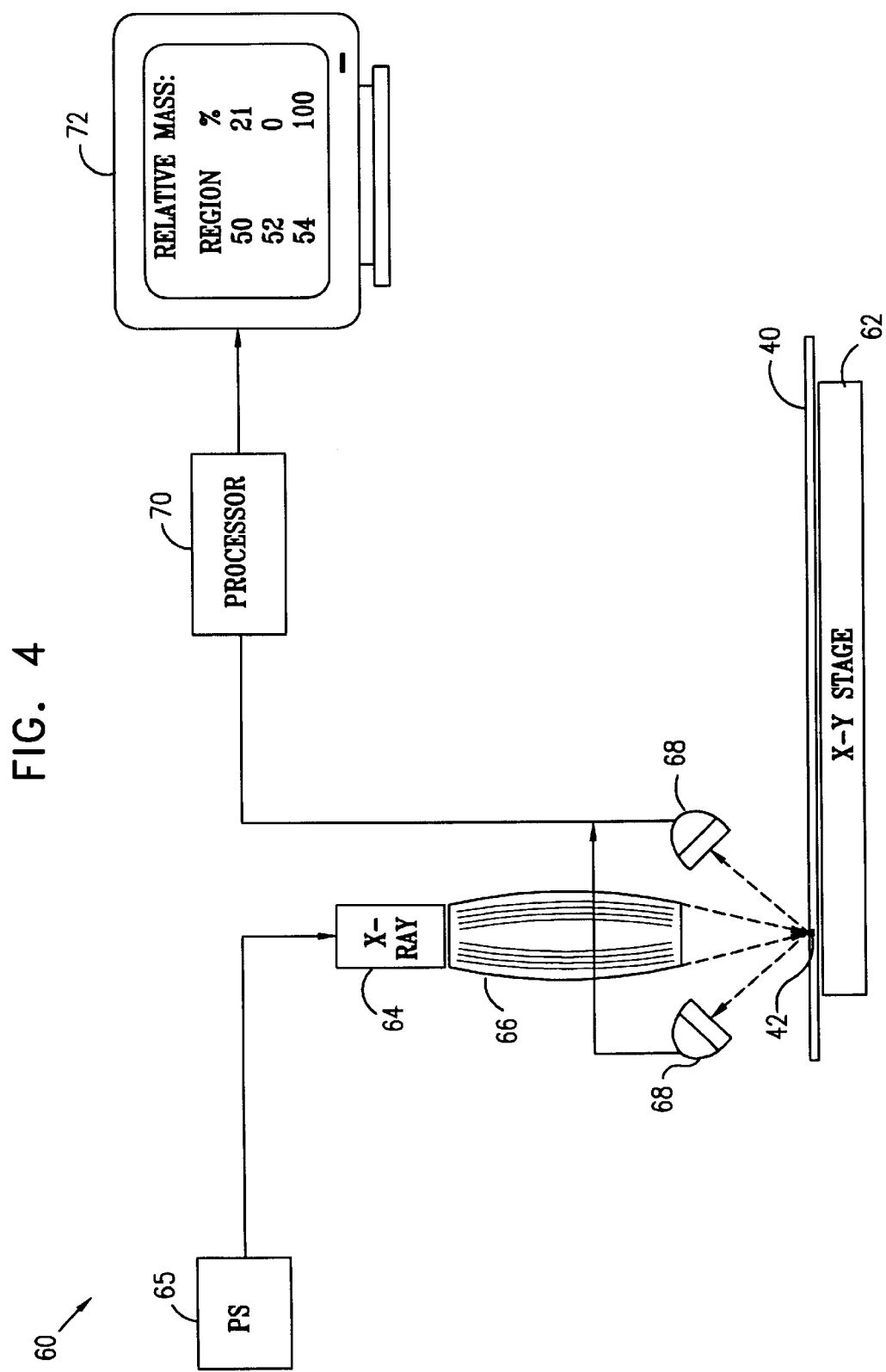
FIG. 4 is a schematic side view of an X-ray microfluorescence analyzer used in testing the wafer of FIG. 2, in accordance with a preferred embodiment of the present invention.

FIG. 4 is a schematic side view of an X-ray microfluorescence analyzer 60, used to evaluate the deposition of material in test pattern 42, in accordance with a preferred embodiment or the present invention. Analyzer 60 is preferably of a type described in U.S. patent application Ser. No. 09/114,789, which is assigned to the assignee of the present patent application, and whose disclosure is incorporated herein by reference. In brief, a microfocus X-ray tube 64, driven by a high-voltage power supply 65, as is known in the art, emits X-rays having a suitable energy range and power flux into X-ray optics 66. The optics preferably comprise a polycapillary array, as described in the above-mentioned patent application, but alternatively, any other suitable X-ray optics known in the art may be used for this purpose. Further alternatively, other types of excitation sources known in the art, such as an energetic ion beam or electron beam, or X-ray sources of other types, may be used in place of tube 64 and its associated power supply and optics.

Optics 66 focus the X-rays onto a small spot, preferably no more than about 50 $\mu$m across, on the surface of wafer 40. The small focal spot enables regions 50 52 and 54 to be irradiated selectively, while minimizing both the amount of wafer "real estate" required for pattern 42 and the time required for the evaluation. Preferably, the dimensions of the X-ray spot size and of the features of test pattern 42, such as recesses 56, are chosen so that measurements using analyzer 60 are relatively insensitive to small lateral displacements of the spot relative to the test pattern. As a result, the X-ray spot can be aligned on the pattern without the need for highly accurate pattern recognition and positioning equipment.

The irradiated area of the water emits fluorescent X-rays, which are captured by an array of detectors 68, preferably four or more such detectors arranged around the focal spot and angled toward the spot. Detectors 68 generate electrical signals, responsive to the captured photons, which are, conveyed to a processor 70. The processor preferably comprises a multichannel, energy-dispersive pulse processing system, as is known in the art, which determines an intensity spectrum of the X-ray photons captured by the detectors. Alternatively, a wavelength-dispersive X-ray detection and processing system may be used. Each element within the focal spot that is excited by the X-rays from tube 64 emits X-rays in characteristic spectral lines. The intensity of the characteristic spectral lines of a given element is proportional to the mass of that element within the focal spot. Thus, processor 70 uses the determined intensity spectra to determine how much of a particular material, such as tantalum and/or copper, is present within the area of the focal spot. The results are displayed on a monitor 72, or may be otherwise printed out and/or stored.

As shown in FIG. 4, microfluorescence analyzer 60 is used to examine test pattern 42 on wafer 40. Preferably, the wafer is mounted on a movable platform, such as an X-Y stage, so as to enable regions 50, 52 and 54 of the pattern to be examined in turn. Alternatively, tube 64, optics 66 and detectors 68 are scanned over the wafer. Preferably, analyzer 60 is used to find the relative concentrations of copper in the different regions by measuring the intensity of one or more characteristic lines in the copper spectrum, such as the Cu K-alpha line. Region 52 is expected to, yield substantially no radiation in these lines and can therefore be used to provide a zero baseline level or background subtraction Region 54, with a known amount of copper in coating 58, provides a full-scale calibration point.

The intensity of the copper lines obtained from region 50, normalized to the intensity obtained from region 54, is proportional to the absolute amount of copper in region 50. As long as recesses 56 are fully filled with the copper, the amount of copper in region 50, relative to that in region 54, should be proportional to the volume of recesses 56, relative to the known volume of coating 58. The intensity of the copper line emission from region 50 will then be in the same, correct proportion to the intensity obtained from region 54, as given by the following formula:

$$\frac{\text{Net\_Intensity(region\_50)}}{\text{Volume(recesses\_56)}} = \frac{\text{Net\_Intensity(region\_54)}}{\text{Volume(copper\_layer)}}$$

Here the "net intensity" is preferably obtained by subtracting a background level, such as that obtained from region 52, from the respective measured intensity in region 50 or 54. The volume of the recesses is preferably verified in advance, using metrology tools known in the art.

If there are voids inside the copper in recesses 56, however, there will be relatively less total copper in region 50. Thus, if the intensity of the copper line emission from region 50 is less than the expected, correct proportion of the intensity obtained from region 54, as given by the equation above, it is an indication that there may be voids in the copper. Preferably, analyzer 60 is programmed with the correct proportion, and notifies an operator of the analyzer when the intensity of the emission from region 50 is such as to indicate a deficiency of copper in the region.

Analyzer 60, in conjunction with test pattern 42, or with other patterns adapted for other purposes, may similarly be used to determine properties of other types of layers formed in the recesses of a semiconductor wafer or other sample. For example, pattern 42 may also be used in step coverage measurements, such as to determine whether tantalum layer 26 (FIG. 1) is of the appropriate thickness. The tantalum measurement is important in order to ensure that the barrier layer is thick enough to protect the underlying dielectric from contamination by copper, but not so thick as to substantially displace the copper in via 32.

The step coverage measurement is preferably made in the following manner. As long as the depth of recesses 56 is known, it is possible to calculate how much tantalum there should be in region 50 if the tantalum layer inside the recesses is of the proper thickness. The depth of the recesses may be known a priori, or it may be determined by optical measurement of ILD 24, as is known in the art. The intensity of the tantalum emission spectrum from region 50 is then compared to that from region 54 (where the quantity of tantalum is also, known) in order to determine whether there is the appropriate amount of tantalum in the recesses, or whether there is too much or too little. The determination of the thickness of tantalum layer 26 is preferably made in this manner before copper layers 28 and 30 are applied. On the other hand, because X-rays can penetrate the copper, measurement of the tantalum layer can also be made after application of the copper, and the copper and tantalum measurements can thus be made simultaneously.

Whereas the measurement methods described hereinabove make use of a special pattern 42, in other preferred embodiments of the present invention, comparable measurements are made on actual device features, such as vias, trenches and contact structures, in dice 44 (FIG. 2). The measured fluorescence intensity is analyzed in a manner similar to that described above in order to determine whether voids have formed in filled recesses in the active device area. Making these measurements on the device area, rather than in the test region, can also provide other essential information about the manufacturing process, such as thickness uniformity at the device level for both materials deposition and removal stages. The accuracy of measurements made in the active device area may be compromised, however, by underlying structures formed in previous process stages.

In one such preferred embodiment, a test pattern is verified a priori and independently. This test pattern is used as reference for all subsequent measurements on production wafers, eliminating the need to create the known test structure on the production wafers.

Although preferred embodiments are described hereinabove with particular reference to semiconductor wafer processing, it will be appreciated that the principles of the present invention may similarly be applied to detect other types of process faults, as well. For example, nearly all conventional packages for integrated circuits and other microelectronic devices use electronic molding compounds to protect chip circuitry and interconnects from the environment. Cured molding compounds may contain defects, such as voids, cracks and particle-related defects, some of which can have an impact on device reliability. X-ray microfluorescence analyzer 60 and the methods described herein may be used, mutatis mutandis, to detect these defects non-destructively.

It will be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for testing the deposition of a material within a recess on the surface of a sample, comprising:

directing an excitation beam onto a region of the sample in a vicinity of the recess;

measuring an intensity of X-ray fluorescence emitted from the region in a spectral range in which the material is known to fluoresce; and determining a quantity of the material that is deposited within the recess responsive to the measured intensity.

2. A method according to claim 1, wherein determining the quantity of the material within the recess comprises detecting a void formed within the material in the recess.

3. A method according to claim 1, wherein determining the quantity of the material comprises determining a thickness of a layer of the material deposited in the recess.

4. A method according to claim 1, wherein directing the excitation beam comprises directing the beam at a test region and a reference region of the sample, and wherein measuring the intensity of X-ray fluorescence comprises comparing the fluorescence from the test region to fluorescence received from the reference region.

5. A method according to claim 4, wherein the test region contains the recess, and wherein the reference region has substantially no recesses in its surface.

6. A method according to claim 1, wherein determining the quantity of the material comprises analyzing the measured fluorescence responsive to a known depth of the recess.

7. A method according to claim 1, wherein the sample comprises a semiconductor wafer, and the recess comprises a microscopic recess etched into the surface of the wafer.

8. A method according to claim 7, wherein the material deposited in the recess comprises a metal.

9. A method according to claim 8, wherein irradiating the region comprises irradiating a pattern of recesses formed in a test region on the water so as to determine how completely the metal has filled vias etched into the surface of the wafer.

10. A method according to claim 1, wherein directing the excitation beam comprises irradiating the region of the sample with X-rays.

11. Apparatus for testing the deposition of a material within a recess on the surface of a sample, comprising:

an excitation source, configured to direct an excitation beam onto a region of the sample in a vicinity of the recess;

one or more X-ray detectors, configured to receive X-ray fluorescence emitted from the region and to generate signals responsive to the received fluorescence; and a processor, coupled to receive the signals from the one or more detectors and to measure, responsive to the signals, an intensity of the fluorescence in a spectral range in which the material is known to fluoresce, so as to determine a quantity of the material that is deposited within the recess.

12. Apparatus according to claim 11, wherein the apparatus is configured to detect a void formed within the material in the recess.

13. Apparatus according to claim 11, wherein the apparatus is configured to determine a thickness of a layer of the material deposited in the recess.

14. Apparatus according to claim 11, wherein the excitation source comprises an X-ray source with X-ray optics, which focus irradiation from the source onto the region.

15. Apparatus according to claim 14, wherein the apparatus is further configured to translate a focal point of the irradiation over the surface of the sample.

16. Apparatus according to claim 14, wherein the sample includes a test region, containing the recess, and a reference region having substantially no recesses in its surface, and wherein the processor is adapted to compare the intensity of the fluorescence from the test region to intensity of fluorescence received from the reference region.

17. Apparatus according to claim 11, wherein the sample comprises a semiconductor wafer, and the recess comprises a microscopic recess etched into the surface of the wafer.

18. A semiconductor wafer, comprising a surface layer in which a test pattern is formed, the test pattern comprising:

a test region, having a plurality of recesses formed in a surface layer thereof, in which recesses a material is deposited during production of semiconductor devices on the wafer; and a reference region, substantially without recesses.

19. A wafer according to claim 18, wherein a comparative measure of X-ray fluorescence emitted from the test region, relative to X-ray fluorescence emitted from the reference region, is indicative of a volume of the material deposited in the recesses.

20. A wafer according to claim 19, wherein the comparative measure is indicative of the occurrence of voids within the material deposited in the recesses.

21. A wafer according to claim 19, wherein the comparative measure is indicative of a thickness of the material deposited within the recesses.

* * * * *